(12) United States Patent
Brandenstein et al.

(10) Patent No.: US 7,441,960 B2
(45) Date of Patent: Oct. 28, 2008

(54) BEARING ARRANGEMENT FOR A MEDICAL DEVICE

(75) Inventors: Manfred Brandenstein, Euβenheim (DE); Heinz Breunig, Aschaffenburg (DE); Jurgen Neder, Schweinfurt (DE); Gunter Neder, Schweinfurt (DE); Armin Olschewski, Schweinfurt (DE)

(73) Assignee: AB SKF, Göteborg (SE)

( * ) Notice: Subject to any disclaimer, the term of this patent is extended or adjusted under 35 U.S.C. 154(b) by 298 days.

(21) Appl. No.: 11/313,653

(22) Filed: Dec. 22, 2005

(65) Prior Publication Data

US 2006/0159379 A1     Jul. 20, 2006

(30) Foreign Application Priority Data

Dec. 23, 2004   (DE) .................... 10 2004 062 116

(51) Int. Cl.
*F16C 27/00* (2006.01)
(52) U.S. Cl. .................. 384/535; 384/538; 384/582
(58) Field of Classification Search ............. 384/99, 384/485, 535–538, 518, 542, 585; 248/634–635; 411/339; 464/68.41
See application file for complete search history.

(56) References Cited

U.S. PATENT DOCUMENTS

| | | | | |
|---|---|---|---|---|
| 2,414,335 | A | | 1/1947 | Schroeder |
| 3,142,520 | A | * | 7/1964 | Mueller ...................... 384/485 |
| 3,460,873 | A | * | 8/1969 | Roney ......................... 384/535 |
| 3,807,820 | A | * | 4/1974 | Schuhmann ................. 384/538 |
| 4,453,783 | A | * | 6/1984 | Davis et al. .................... 384/99 |
| 4,639,150 | A | | 1/1987 | Habermann |
| 4,664,536 | A | * | 5/1987 | Kamman ...................... 384/99 |
| 4,890,709 | A | * | 1/1990 | Reik et al. ............... 464/68.41 |
| 5,110,081 | A | * | 5/1992 | Lang, Jr. ..................... 248/635 |
| 5,174,661 | A | * | 12/1992 | Nicolas et al. .............. 384/538 |
| 5,564,903 | A | | 10/1996 | Eccles et al. |
| 5,868,503 | A | | 2/1999 | Bade |
| 6,099,165 | A | * | 8/2000 | Tremaine ..................... 384/99 |
| 6,227,715 | B1 | * | 5/2001 | Erhardt et al. .............. 384/518 |
| 6,471,179 | B1 | * | 10/2002 | Tousi et al. ................. 248/635 |
| 6,485,241 | B1 | * | 11/2002 | Oxford ........................ 411/339 |

(Continued)

FOREIGN PATENT DOCUMENTS

DE       69 05 044 U       6/1947

(Continued)

OTHER PUBLICATIONS

Germany Office Action dated May 12, 2005 and English language translation.

*Primary Examiner*—Marcus Charles
(74) *Attorney, Agent, or Firm*—Buchanan Ingersoll & Rooney PC

(57) ABSTRACT

A bearing arrangement for a medical device in which a rotating component is supported relative to a stationary housing includes a bearing with an inner ring and an outer ring. The inner ring is connected to the component which is to be supported and the outer ring is connected to the housing by way of at least one damping element. To increase quiet running of the rotating component, both the inner ring and also the outer ring are made as integral elements and have an essentially hollow cylindrical base contour, with an extension of the outer ring in the radial direction being at least twice the extension of the inner ring in the radial direction.

24 Claims, 5 Drawing Sheets

U.S. PATENT DOCUMENTS

| | | | |
|---|---|---|---|
| 6,880,977 B2 * | 4/2005 | Seufert | 384/446 |
| 2005/0053318 A1 * | 3/2005 | Casey | 384/538 |

FOREIGN PATENT DOCUMENTS

| | | |
|---|---|---|
| DE | OS 15 75 635 | 2/1970 |
| DE | PS 78 523 | 2/1970 |
| DE | 70 18 297 U | 5/1970 |
| DE | 30 32 820 C2 | 4/1982 |
| DE | 35 11 480 C1 | 6/1986 |
| DE | 25 55 021 C2 | 6/1997 |
| DE | 196 45 530 C2 | 5/1998 |
| DE | 695 07 576 T2 | 7/1999 |
| DE | 200 11 947 U1 | 1/2001 |
| DE | 10235287 A1 * | 2/2004 |
| DE | 10235290 A1 * | 2/2004 |
| FR | 1.296.932 | 8/1961 |
| FR | 2703415 A1 * | 10/1994 |
| GB | 412 491 | 9/1933 |
| GB | 908631 | 8/1961 |
| GB | 2 082 525 A | 7/1981 |
| JP | 02-172446 A * | 7/1990 |
| WO | WO 02/27 203 A1 | 4/2002 |

* cited by examiner

US 7,441,960 B2

BEARING ARRANGEMENT FOR A MEDICAL DEVICE

CROSS REFERENCE TO RELATED APPLICATION

This application is based on and claims priority under 35 U.S.C. § 119(a) with respect to German Application No. 10 2004 062 116.0 filed on Dec. 23, 2004, the entire content of which is incorporated herein by reference.

FIELD OF THE INVENTION

The invention generally relates to a bearing arrangement. More specifically, the invention pertains to a bearing arrangement for a medical device, with which a rotating component is supported relative to a stationary housing, and wherein the bearing arrangement comprises a bearing with an inner ring connected to the component which is to be supported and an outer ring connected to the housing. The disclosed bearing arrangement has particularly useful application in computer tomographs.

BACKGROUND OF THE INVENTION

In the case of computer tomographs in particular, it is necessary to support a drum-shaped body relative to the housing such that it can be turned around an axis of rotation for purposes of preparation of tomographic images. To irradiate a patient who is to be examined, an x-ray tube is placed in the drum-shaped body and on the side of the drum diametrically opposite the x-ray tube, radiation detectors which receive the emitted x-radiation are provided.

A bearing arrangement described in the context of an electrical machine is disclosed in DE-OS 15 75 635. Here the outer ring of the bearing is connected to the housing or the frame by way of a damping element or by way of several damping elements which are arranged in a uniformly distributed manner over the periphery of the outer bearing ring. The inner ring of the bearing carries the turning component.

Other publications such as DD-PS 78 523, DE 25 55 021 C2 and DE 30 32 820 C2 disclose bearings for diverse applications in which elastomer blocks or sleeves consisting of elastomer material are used to impart an improved damping property to the bearing.

A roller bearing for a nuclear spin tomograph with magnetic roll bodies and with an inner ring and outer ring between which the roll bodies can roll is described in WO 02/27203 A1. This document describes that the outer ring is surrounded by a nonmagnetic ring.

For computer tomographic systems, bearing arrangements are known in which wire bearings with inserted damping elements are used. Therefore the rotary drum is supported there by way of a ball bearing with traverse wires, the traverse wires being placed in damping plastic inserts. In addition, ceramic balls are used as the roll bodies for the bearing.

It has been found that existing bearing systems especially in computer tomographs still do not meet necessary of desired requirements because the bearing arrangement in operation (when the drum is turning) has relatively high noise development. It is thus hardly possible to meet the requirement for a quiet bearing which produces at most 55 dB(A). The damping of the bearing arrangement therefore has been inadequate for a long time.

Another problem also linked to noise development is that the rotating drum in operation has a not inconsiderable ovalness. That is, the bearing has not been able to grip and support the drum such that it retains a largely round shape.

SUMMARY

According to one aspect, a bearing arrangement is provided in a medical device in which a rotating component is supported relative to a stationary housing. The bearing arrangement comprises a bearing that includes an inner bearing ring and an outer bearing ring, with the inner bearing ring being connected to the component which is to be supported and the outer ring being connected to the housing by way of at least one damping element. Both the inner bearing ring and the outer bearing ring are made as integral one-piece elements possessing a hollow cylindrical base contour, and a radial extension of the outer bearing ring in the radial direction is at least twice the radial extension of the inner bearing ring in the radial direction The bearing arrangement here has particularly useful application in the case of a medical device in the form of a computer tomograph. The drum of such a computer tomography possesses relatively low inherent stiffness. The drum is gripped by the thin-walled inner ring of the bearing, with a high level of roundness being imparted to the inner ring by the outer ring which is made stiff in relation, and as a result also to the drum, so that relatively quiet running of the bearing arrangement is possible.

Preferably the extension of the outer ring in the radial direction is even at least three times that of the inner ring in the radial direction. Advantageously here, the extension of the inner ring in the radial direction is between 15 mm and 30 mm, and the inside diameter of the inner ring being between 1000 and 2000 mm.

The bearing is advantageously made as a roller bearing in which roll bodies, preferably balls, are located between the inner ring and outer ring. Preferably the inner ring, the outer ring, and the roll bodies located in between are subject to tolerances such that there is prestress in the bearing.

The bearing arrangement can include a plurality of damping elements arranged and distributed equidistantly over the periphery of the outer bearing ring.

The damping element can be located in at least one recess in the outer ring, with the damping element and the recess being complementarily shaped such that the damping element in the installed state continues or supplements the hollow cylindrical base contour of the outer ring. Here, at least one recess in the outer ring preferably has an arc-shaped boundary or periphery as seen in the axial direction, especially a circular arc-shaped boundary.

Very good damping with simultaneously adequate stiffness can be achieved in that the damping element extends from the surface of contact with the housing in the axial direction between 30% and 70% of the axial width of the outer ring.

In addition, good linkage of the outer ring to the housing can be produced by the extension of the damping element in the axial direction being greater than the axial width of the recess in the outer ring for holding the damping element. Preferably, the extension of the damping element in the axial direction is between 102% and 107% of the axial width of the recess in the outer ring.

It is also possible to provide damping elements in the two axial end areas of the outer ring in respective recesses. The outer ring is therefore bordered on either side by the damping elements and linked to the housing by way of the damping elements.

To fix the outer ring on the housing, fasteners are preferably provided and extend in the axial direction through the outer ring, the damping element or damping elements and the housing. The fasteners can be in the form of screws.

The damping elements can be protected from the outside by covering the damping element or damping elements with a covering part which extends over part of the outer periphery of the outer ring and is fixed (e.g., screwed down) on the outer bearing ring.

The presence of sufficient prestress in the bearing benefits the centering action which the outer ring of the bearing, which is made relatively solid, applies to the drum, which has relatively little inherent stiffness, by way of the roll bodies and the inner ring. Therefore, the bearing arrangement also preferably includes means for setting the prestress in the bearing. This means can be formed by a conical sleeve which adjoins one of the bearing rings and which is arranged to be able to move adjustably in the axial direction. The conical sleeve preferably interacts with the inner ring, and is preferably located between the component and the inner ring. Installation can be simplified if the conical sleeve is formed by individual segments arranged bordering one another in the peripheral direction.

The conical sleeve can be made of plastic. Rubber or elastomer material, especially thermoplastic or duroplastic, has proven suitable as the material for the damping element. Also, while the bearing rings can consist of conventional ball bearing steel, it is also possible for them to consist of nonmagnetic material.

The bearing arrangement here is especially quiet and is designed to provide relatively uniform running. The bearing arrangement, especially when used in applications having parts which are to be supported and which have relatively low inherent stiffness, helps provide good concentricity and thus contributes to increased quiet running. The bearing arrangement has particularly useful application in the context of a medical device such as a computer tomograph having a drum-shaped component which is to be supported and which has a relatively low inherent stiffness. When applied to a computer tomography, noise development by the bearing arrangement here of less than 55 dB(A) is possible. The drum-shaped component which is to be supported has an inherent stiffness which is low relative to the stiffness of the outer ring of the bearing. The drum of the tomograph to be supported is held well centered by the bearing arrangement so that the ovalness of the drum is relatively low. Also, vibrations acting on the system are well damped both in the axial and the radial direction.

BRIEF DESCRIPTION OF THE DRAWING FIGURES

The foregoing and additional features and characteristics of the disclosed subject matter will become more apparent from the following detailed description considered with reference to the accompanying drawing figures in which like reference numerals designate like elements.

DETAILED DESCRIPTION

Figure 1:
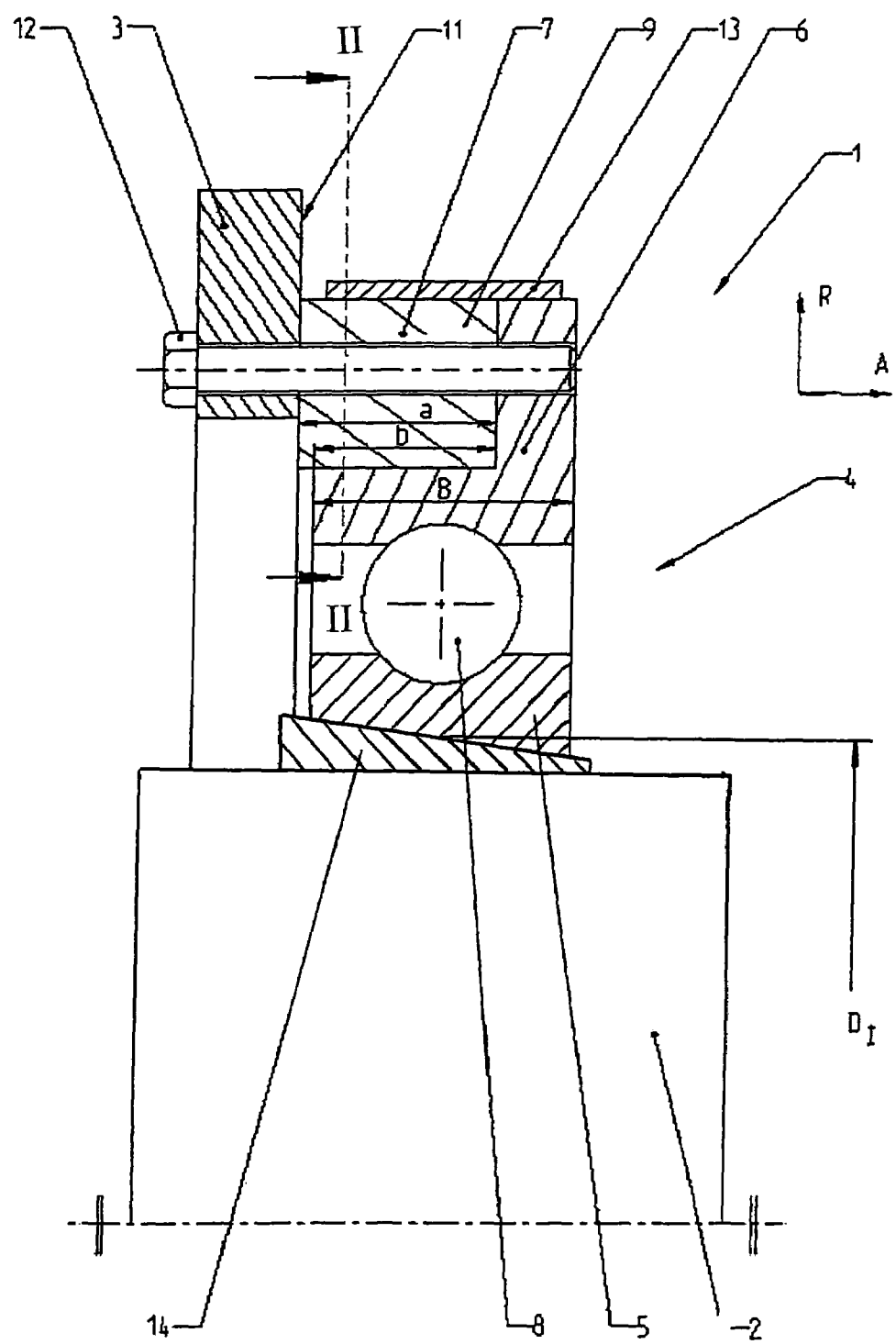
FIG. 1 is a cross-sectional view of a top half of the bearing arrangement along the section line I-I in FIG. 2.

Referring to FIG. 1, the bearing arrangement 1 supports a rotating component 2 in the form of the drum of a computer tomograph relative to the stationary housing 3. The component 2 is relatively thin-walled for reasons of weight and so it tends slightly to exhibit or experience unwanted ovalness.

The component 2 is supported by the bearing arrangement which includes a bearing 4. In the illustrated embodiment, the bearing is in the form of a single-row deep groove ball bearing. However, it is to be understood that other bearing types can also be employed. The bearing 4 comprises an inner bearing ring 5 and an outer bearing ring 6 between which are arranged roll bodies 8 in the form of balls in a conventional manner. Depending on requirements, the balls 14 consist either of steel or of ceramic. The inner and outer bearing rings 5, 6 are preferably made of nonmagnetic material.

As the FIG. 1 cross-section illustrates, both the inner ring 5 and also the outer ring 6 are made as integral one-piece elements. That is, they each consist of a one-piece ring. Here the entire bearing 4 is made as a so-called heavy bearing in which the outside diameter of the outer ring 6 is greater than roughly 400 mm. Both the inner bearing ring 5 and also the outer bearing ring 6 possess an essentially hollow cylindrical base contour. The inner ring 5 is made relatively thin-walled relative to the outer ring 6. The extension of the outer bearing ring 6 in the radial direction R is at least twice, preferably at least three times, the extension of the inner bearing ring 5 in the radial direction R.

In the embodiment the radial extension (thickness) of the inner ring 5 is roughly 15 mm to 30 mm, while the inside diameter $D_I$ of the inner ring 5 is between 1000 mm and 2000 mm.

Figure 2:
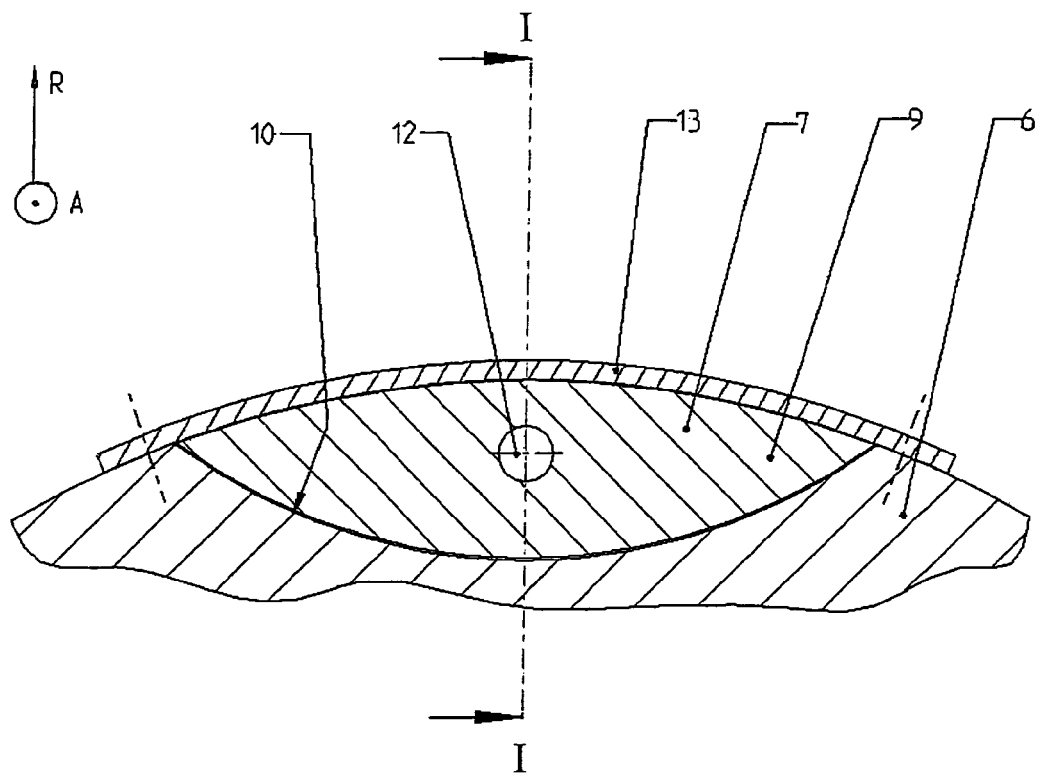
FIG. 2 is a cross-sectional view of the outer ring of the bearing together with the damping element taken along the section line II-II in FIG. 1.
Figure 3:
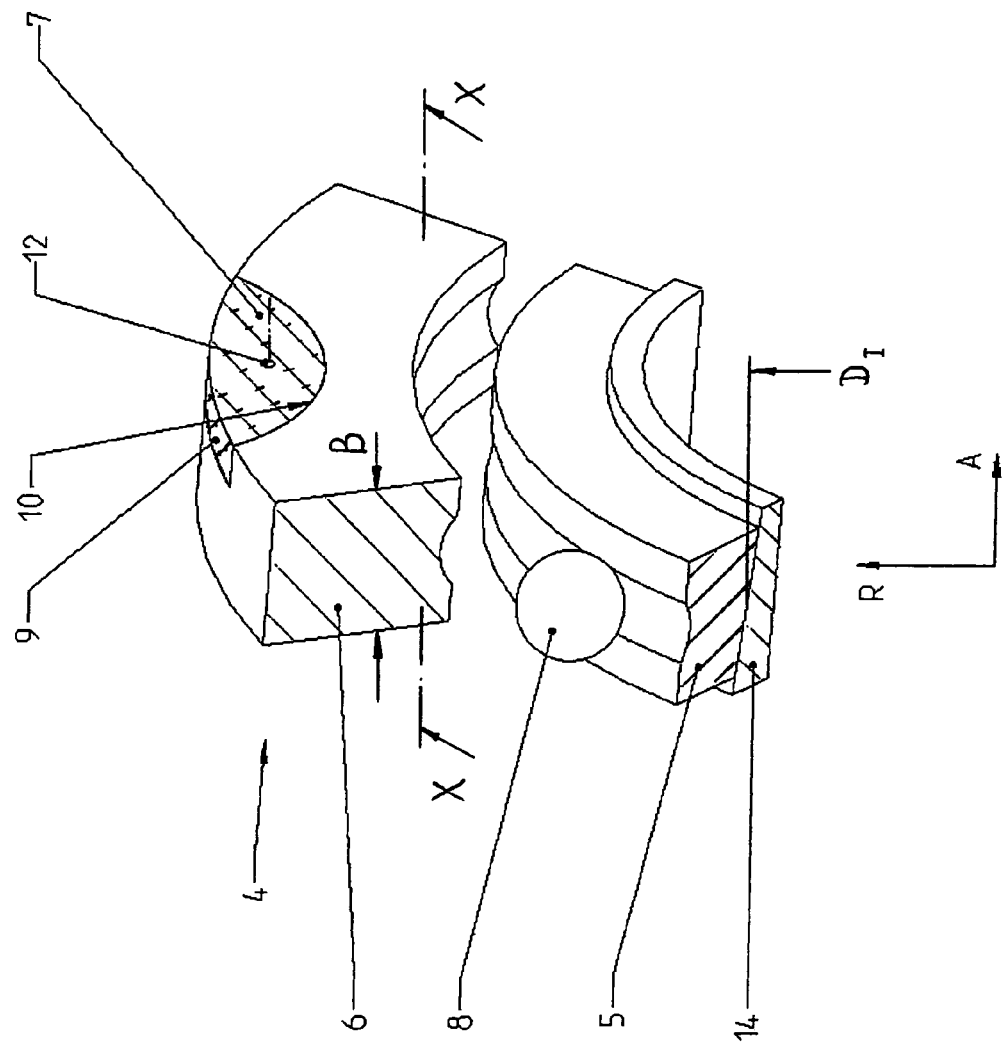
FIG. 3 is a perspective view of a part of the bearing arrangement with partially cutaway parts.

As can be seen from FIGS. 1-3 collectively, the outer bearing ring 6 has, at several peripheral points, for example at four, five or six points of the periphery, a recess 9 into which one damping element 7 is inserted. The plurality of damping elements 7 are preferably distributed equidistantly over the periphery of the outer bearing ring. The damping elements 7 in the recesses 9 establish the connection between the outer ring 6 and the housing 3. Screws 12 which are aligned in the axial direction A penetrate and brace the housing 3, the damping element 7 and the outer bearing ring 6 as schematically illustrated. As best depicted in FIG. 2, the recess 9 for each damping element 7 has an arc-shaped (e.g., circular arc-shaped) boundary 10. The damping element 7 is in turn shaped such that after it is inserted into the recess 9 it fills the recess such that a largely undisrupted hollow cylindrical contour for the outer ring 6 results. Thus, the damping element and the recess are shaped such that the damping element in the installed state continues or supplements the hollow cylindrical base contour of the outer ring 6. The damping elements are preferably made of rubber or of an elastomer material, and more preferably are made of thermoplastic or duroplastic.

FIG. 1 shows that the recess 9 in the outer bearing ring 6 possesses a width b in the axial direction A which corresponds to roughly two-thirds of the axial width B of the outer bearing ring 6. However, the damping element 7 which is to be inserted has, at least in the uninstalled and unstressed state, an axial extension or dimension a which is slightly greater than the width b so that the damping element 7 projects slightly beyond (i.e., to the left) of the side face of the outer ring 6. The extension a of the damping element 7 in the axial direction A is preferably between 102% and 107% of the axial width b of the recess 9 in the outer ring 3. The projecting part of the damping element 7 adjoins the facing contact surface 11 of the housing 3 such that contact between the housing 3 and the outer ring 6 can be established in this way entirely by way of the damping element 7. When the screw 12 is tightened, the damping element 7 is compressed and the side surface of the outer bearing ring 6 contacts the contact surface 11 on the housing 3. The damping element 7 extends from the surface 11 of contact with the housing 3 in the axial direction A between 30% and 70% of the axial width B of the outer ring 6.

Each damping element 7 can be covered by a covering part 13 as shown in FIGS. 1 and 2. The covering part 13 can be fixed to the outer periphery of the outer bearing ring 6 (e.g., screwed down on the outer periphery of the outer bearing ring 6). The covering part preferably extends over a certain peripheral section of the outer ring 6.

Optimum support of the drum 2, which has relatively little inherent stability, by the bearing arrangement 1 arises by the inner bearing ring 5 of the bearing 4, which inner bearing ring has equally little inherent stiffness, and which interacts with the stable outer ring 6 which is made very solid in relation thereto. By way of prestress of the bearing 4 (i.e. by way of pressing between the outer ring 6, the balls 8 and the inner ring 5), the inner ring 5 and as a result also the drum 2 are pressed round so that any ovalness in the drum in the supported state is relatively low.

Figure 5:
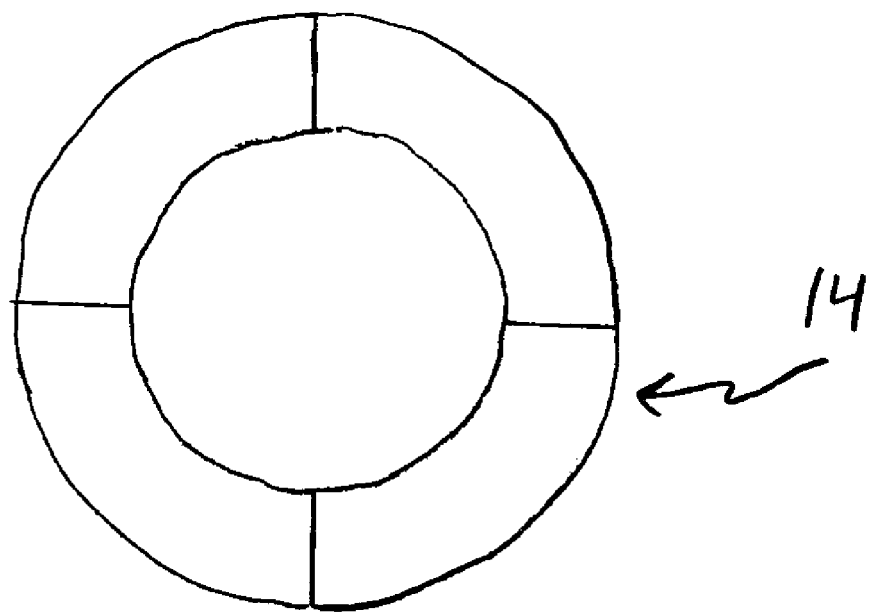
FIG. 5 is an end view of the conical sleeve forming a part of the bearing arrangement, illustrating one possible form of the conical sleeve comprising four separate segments.

So that sufficient prestress is present in the bearing 4, the bearing arrangement is provided with means 14 for setting the prestress in the bearing. In this illustrated embodiment, this prestress setting means 14 is in the form of a conical sleeve which interacts with the radially inner surface of the inner ring 5 which is likewise made conical. The desired amount of prestress in the bearing 4 can be set in a known manner by axially adjusting the conical sleeve 14 (i.e., moving the sleeve in the axial direction A) relative to the inner ring 5. The conical sleeve can be made of plastic material. In addition, the conical sleeve 14 can be formed by individual segments (e.g., four segments) arranged to border one another in the peripheral direction. FIG. 5 illustrates an example of a conical sleeve formed by four separate segments.

Figure 4:
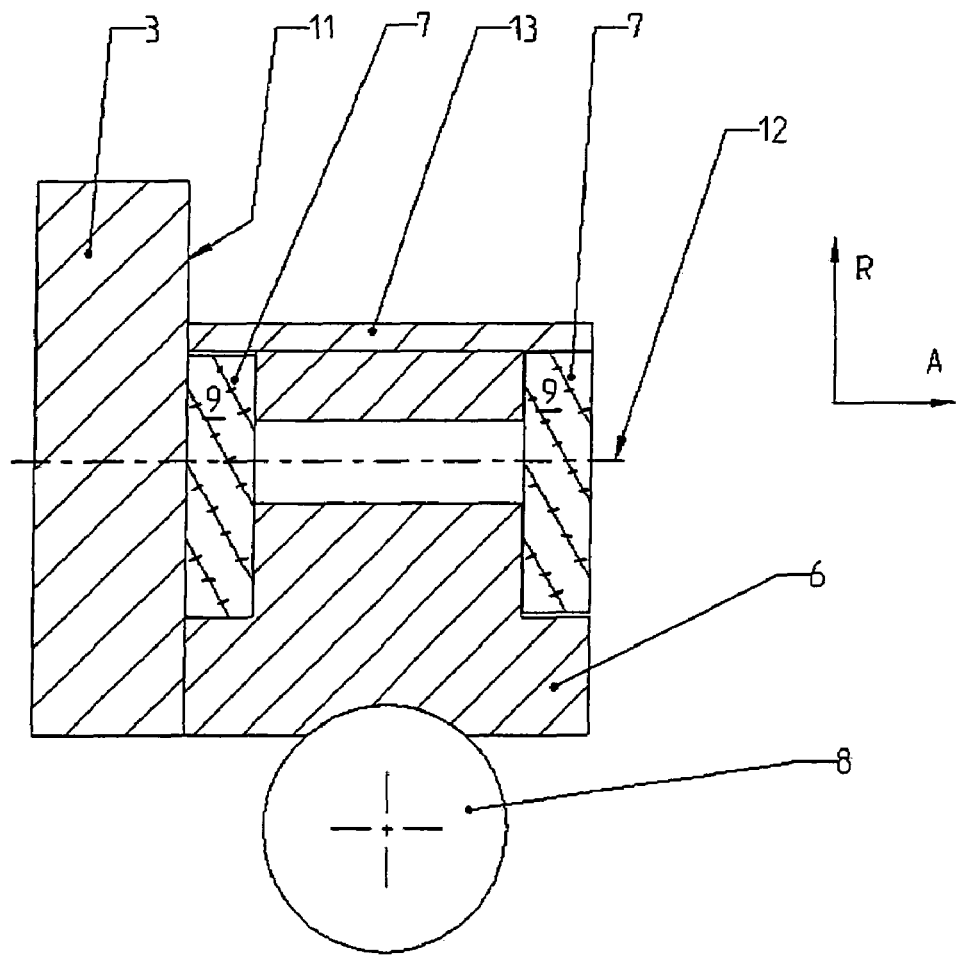
FIG. 4 is a cross-sectional view of another embodiment of the outer ring of the bearing together with the damping elements.

FIG. 4 shows an alternative embodiment. In this embodiment, both outer axial end areas of the outer bearing ring 6 are provided with a recess 9 into which a respective damping element 7 is inserted. Several of these recesses 9 and damping elements 7 are distributed over the periphery of the outer bearing ring 6 at each axial end. With this approach, softer or more damped linkage of the outer ring 6 to the housing 3 becomes possible.

To achieve an even more optimum noise reduction, the roll body tracks in the outer and inner bearing rings after grinding can be honed or tumbled. That is, after grinding there is further precision machining in order to achieve the best possible results.

The principles, preferred embodiments and manners of use of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. Bearing arrangement in a computer tomograph in which a rotating component is supported relative to a stationary housing, the bearing arrangement comprising a bearing that comprises an inner bearing ring and an outer bearing ring, the inner bearing ring being connected to the component which is to be supported and the outer ring being connected to the housing by way of at least one damping element configured to damp vibration between the outer bearing ring and the stationary housing, both the inner bearing ring and the outer bearing ring are made as integral one-piece elements possessing a hollow cylindrical base contour, a radial extension of the outer bearing ring in the radial direction being at least twice the radial extension of the inner bearing ring in the radial directions, wherein the component which is to be supported is drum-shaped and has a stiffness which is low relative to the stiffness of the outer bearing ring of the bearing, and wherein the radial extension of the inner bearing ring in the radial direction is between 15 mm and 30 mm, and an inside diameter of the inner bearing ring is between 1000 and 2000 mm.

2. Bearing arrangement in a computer tomograph according to claim 1, wherein the radial extension of the outer bearing ring in the radial direction is at least three times the radial extension the inner bearing ring in the radial direction.

3. Bearing arrangement in a computer tomograph according to claim 1, wherein the bearing is a roller bearing and comprises roll bodies positioned between the inner bearing ring and the outer bearing ring.

4. Bearing arrangement in a computer tomograph according to claim 3, wherein the inner bearing ring, the outer bearing ring, and the roll bodies located in between are subject to tolerances such that there is prestress in the bearing.

5. Bearing arrangement in a computer tomograph according to claim 1, comprising a plurality of damping elements distributed equidistantly over a periphery of the outer bearing ring.

6. Bearing arrangement in a computer tomograph according to claim 1, wherein the at least one damping element is located in at least one recess in the outer bearing ring, the at least one damping element and the recess being shaped such that the damping element in the installed state continues the hollow cylindrical base contour of the outer bearing ring.

7. Bearing arrangement in a computer tomograph according to claim 6, wherein the at least one damping element and the at least one recess are positioned at one end of the outer bearing ring, and comprising another damping element positioned in another recess at an opposite end of the outer bearing ring.

8. Bearing arrangement in a computer tomograph according to claim 6, further comprising at least one fastener extending axially through the outer bearing ring, the at least one damping element and the housing to fix the outer bearing ring on the housing.

9. Bearing arrangement in a computer tomograph according to claim 6, wherein the at least one recess in the outer bearing ring, seen in an axial direction, is arc-shaped.

10. Bearing arrangement in a computer tomograph according to claim 1, wherein the at least one damping element contacts a contact surface of the housing and the outer bearing ring possesses an axial width, the at least one damping element extending axially from the contact surface of the housing between 30% and 70% of the axial width of the outer bearing ring.

11. Bearing arrangement in a computer tomograph according to claim 6, wherein an axial extent of the at least one damping element in an axial direction is greater than an axial width of the at least one recess in the outer bearing ring.

12. Bearing arrangement in a computer tomograph according to claim 11, wherein the axial extent of the at least one damping element in the axial direction is between 102% and 107% of the axial width of the at least one recess.

13. Bearing arrangement in a computer tomograph according to claim 1, wherein the at least one damping element is covered by a covering part extending over part of an outer periphery of the outer bearing ring and fixed to the outer bearing ring.

14. Bearing arrangement in a computer tomograph according to claim 1, further comprising means for setting prestress in the bearing.

15. Bearing arrangement in a computer tomograph according to claim 14, wherein the means for setting prestress comprises an axially movable conical sleeve adjoining one of the inner and outer bearing rings.

16. Bearing arrangement in a computer tomograph according to claim 15, wherein the conical sleeve engages the inner bearing ring.

17. Bearing arrangement in a computer tomograph according to claim 16, wherein the conical sleeve is located between the component and the inner bearing ring.

18. Bearing arrangement in a computer tomograph according to claim 15, wherein the conical sleeve is a plastic conical sleeve.

19. Bearing arrangement in a computer tomograph according to claim 15, wherein the conical sleeve is formed by a plurality of individual segments bordering one another in a peripheral direction.

20. Bearing arrangement in a computer tomograph according to claim 1, wherein the at least one damping element is made of rubber or of an elastomer material.

21. Bearing arrangement in a computer tomograph according to claim 20, wherein the at least one damping element is made of thermoplastic or duroplastic.

22. Bearing arrangement in a computer tomograph according to claim 1, wherein the inner and outer bearing rings are made of nonmagnetic material.

23. A bearing arrangement forming part of a computer tomograph to support a drum of the computer tomograph relative to a housing, the bearing arrangement comprising:
- an inner bearing ring mounted on the drum, the inner bearing ring being a one-piece integral inner bearing ring possessing a hollow cylindrical configuration;
- an outer bearing ring connected to the housing, the outer bearing ring being a one-piece integral outer bearing ring possessing a hollow cylindrical configuration;
- a plurality of roll bodies positioned between the inner bearing ring and the outer bearing ring;
- the outer bearing ring being connected to the housing by way of an damping element;
- the outer bearing ring having a radial extent in the radial direction that is at least twice the radial extent of the inner bearing ring in the radial direction; and
- the damping element being in contact with the housing and the outer bearing ring, and being positioned between facing surfaces of the housing and the outer bearing ring to absorb vibration transmitted between the outer bearing ring and the housing;
- wherein the drum has a stiffness which is low relative to the stiffness of the outer bearing ring of the bearing.

24. A bearing arrangement forming part of a computer tomograph according to claim 23, further comprising a fastener extending through the damping element, the housing and the outer bearing ring to secure together the housing and the outer bearing ring while compressing the damping element.

* * * * *